(12) United States Patent
Pentyala (10) Patent No.: US 7,794,953 B2
(45) Date of Patent: Sep. 14, 2010

(54) METHOD AND KITS FOR DETECTING CEREBROSPINAL FLUID IN A SAMPLE

(75) Inventor: Srinivas N. Pentyala, South Setauket, NY (US)

(73) Assignee: Stony Brook Anaesthesiology, Univeristy Faculty Practice Corporation, Stony Brook, NY (US)

( * ) Notice: Subject to any disclaimer, the term of this patent is extended or adjusted under 35 U.S.C. 154(b) by 0 days.

(21) Appl. No.: 11/789,868

(22) Filed: Apr. 26, 2007

(65) Prior Publication Data

US 2007/0196864 A1    Aug. 23, 2007

Related U.S. Application Data

(60) Division of application No. 11/516,385, filed on Sep. 6, 2006, which is a continuation-in-part of application No. 10/409,758, filed on Apr. 9, 2003, now abandoned.

(51) Int. Cl.
G01N 33/53 (2006.01)
G01N 33/573 (2006.01)

(52) U.S. Cl. .......................... 435/7.1; 435/7.4

(58) Field of Classification Search .................. None
See application file for complete search history.

(56) References Cited

U.S. PATENT DOCUMENTS

| | | | |
|---|---|---|---|
| 4,946,778 A | 8/1990 | Ladner et al. | |
| 4,981,785 A | 1/1991 | Nayak | |
| 5,358,691 A | 10/1994 | Clark et al. | |
| 5,599,677 A | 2/1997 | Dowell et al. | |
| 5,602,040 A | 2/1997 | May et al. | |
| 5,672,480 A | 9/1997 | Dowell et al. | |
| 5,712,170 A | 1/1998 | Kouvonen et al. | |
| 5,885,530 A | 3/1999 | Babson et al. | |
| 6,159,750 A | 12/2000 | Edmonds | |
| 6,180,370 B1 | 1/2001 | Queen et al. | |
| 6,277,969 B1 | 8/2001 | Le et al. | |
| 6,352,862 B1 | 3/2002 | Davis et al. | |
| 6,458,549 B2 | 10/2002 | Maesaka | |
| 6,461,827 B1 | 10/2002 | Oda et al. | |
| 6,605,705 B1 | 8/2003 | Oda et al. | |
| 6,790,635 B1 | 9/2004 | Seiki et al. | |
| 6,867,051 B1 * | 3/2005 | Anderson et al. | 436/518 |
| 7,524,635 B2 | 4/2009 | Buechler | |
| 2002/0141997 A1 | 10/2002 | Nagata | |
| 2004/0002168 A1 | 1/2004 | Remington et al. | |
| 2004/0203079 A1 | 10/2004 | Pentyala | |

FOREIGN PATENT DOCUMENTS

| | | |
|---|---|---|
| WO | WO 93/03367 A1 | 2/1993 |
| WO | 03105899 A1 | 12/2003 |
| WO | WO 2004/091481 A2 | 10/2004 |

OTHER PUBLICATIONS

The American Heritage® Dictionary of the English Language, definition of the term "in situ", (2007), Retrieved Feb. 28, 2008, from http://www.credoreference.com/entry/7071735.*
Filler et al. "Beta-Trace Protein, Cystatin C, Beta-2-Microglobulin, and Creatinine Compared for Detecting Impaired Glomerular Filtration Rates in Children" Clinical Chemistry (2002) 48:5 729-736.*
Chan et al. "Persistent cerebrospinal fluid leak: a complication of the combined spinal-epidural technique" Anesth Analg. Mar. 2004;98(3):828-30.*
Petereit et al. "A new nephelometric assay for β-trace protein (prostaglandin D synthase) as an indicator of liquorrhoea" J Neurol Neurosurg Psychiatry. Sep. 2001; 71(3): 347-351.*
Harlow, E. and Lane, D., Antibodies: A Laboratory Manual (1988) Cold Spring Harbor Laboratory Press, Cold Spring Harbor, NY, pp. 59-61, 72-87, 173-174, 473-480, and 555.*
Waters et al. "Glucose in Epidural Catheter Aspirate" Anesth Analg vol. 76 (1993), pp. 546-548.*
Adsumelli et al. ("Prostaglandin D2 as a Marker for Identification of Cerebrospinal Fluid During Epidural Anesthesia: An In Vitro Study", Feb. 2003 Supplement to Anesthesia & Analgesia, vol. 96, No. S, Abstract No. S-278; also presented at the International Anesthesia Research Society, 77th Clinical and Scientific Congress, Mar. 21-25, 2003.*
Felgenhauer, K., et al., "*Beta Trace-Protein as Marker for Cerebrospinal Fluid Fistula*", Klinische Wochenschrift, vol. 65, pp. 764-768, XP-001246953 (1987).
Arrer, E., et al., "*Beta-Trace Protein as a Marker for Cerebrospinal Fluid Rhinorrhea*", Clinical Chemistry, vol. 48, No. 6, pp. 939-941, XP-002386738 (2002).

(Continued)

Primary Examiner—Mark L Shibuya
Assistant Examiner—Christine Foster
(74) Attorney, Agent, or Firm—Cantor Colburn LLP (57) ABSTRACT

The present invention relates to detection of the presence or absence of cerebrospinal fluid (CSF) in a sample, in particular to the analysis of the CSF protein lipocalin-type prostaglandin D2 synthase (L-PGDS). The present invention provides assays for the analysis of PGDS indicating the presence or absence of CSF in a sample.

2 Claims, 7 Drawing Sheets

OTHER PUBLICATIONS

McArthur, J., et al., "*Cerebrospinal fluid and serum concentrations of beta-trace protein during pregnancy*", Anaesthesia, vol. 60, pp. 163-167, XP-002386740 (2005).

Garcia-Fernández, L. F., et al., "*Dexamethasone Induces Lipocalin-Type Prostaglandin D Synthase Gene Expression in Mouse Neuronal Cells*", Journal of Neurochemistry, vol. 75, pp. 460-470, (2000).

Kitchel, S. H., et al., "*Closed Subarachnoid Drainage for Management of cerebrospinal fluid leakage after an Operation on the Spine*", The Journal of Bone and Joint Surgery, vol. 71-A, No. 7, pp. 984-987 (Aug. 1989).

Bachmann, G., et al., "*Predictive Values of Beta-Trace Protein (Prostaglandin D Synthase) by Use of Laser-Nephelometry Assay for the Identification of Cerebrospinal Fluid*", Neurosurgery, vol. 50, No. 3, pp. 571-576 (2002).

Medline Plus, Drug Information: Lidocaine (Topical), Downloaded from: http://www.nim.nih.gov/medlineplus/druginfo/uspdi/500058.html on Feb. 28, 2006.

Kuczkowski, K.M. and Benumof, J. L., "*Decrease in the incidence of post-dural puncture headache: maintaining CSF volume*", ACTA Anaesthesiologica Scandinavica, vol. 47, pp. 98-100 (2003).

Bachmann, G., et al., "*Clinical Experience with beta-Trace Protein as a Marker for Cerebrospinal Fluid*", The Annals of Otology, Rhinology & Laryngology, vol. 109, No. 12, pp. 1099-1102 (Dec. 2000).

Petereit, H. F., et al., "*A new nephelometric assay for Beta-trace protein (prostaglandin D synthase) as an indicator of liquorrhoea*", Journal of Neurol Neurosurgery Phychiatry, vol. 71, pp. 347-351 (2001).

Köhler, G. and Milstein, C., "*Continuous Cultures of Fused Cells Securing Antibody of Predefined Specificity*," Nature, vol. 2577, pp. 495-497 (1975).

Kozbor, D. and Roder, John C., "*The Production of Monoclonal Antibodies from Human Lymphocytes*", Immunology Today, vol. 4, No. 3, pp. 72-79 (1983).

Cole, S.P.C., Kozbor, D. and Roder, John C., "*Monoclonal Antibodies and Cancer Therapy*", Proceedings of the Roche-UCLA Symposium, pp. 77-96 (1985).

Cote, R. J., et al., "*Generation of Human Monoclonal Antibodies Reactive with Cellular Antigens*", Proceedings of the National Academy of Science, vol. 80, No. 7, pp. 2026-2030 (1983).

Huse, W. D., et al., "*Generation of a Large Combinatorial Library of the Immunoglobulin Repertoire in Phage Lambda*", Science, vol. 246, No. 4935, pp. 1275-1281 (1980).

Adair, J. R. and King, D. J., "*Reconstruction of monoclonal antibodies by genetic engineering*", Bios Scientific Publishers Limited, Chapter 4, pp. 67-92 (2000).

Pietersz, G. A. and McKenzie, F. C., "*The genetic engineering of antibody constructs for diagnosis and therapy*", Bios Scientific Publishers Limited, Chapter 5, pp. 93-117 (2000).

Sanders, E. A., et al., "*Cerebrospinal Fluid Leakage: Agarose Gel Electrophoresis Detection of $B_2$-Transferrin and Nephelometric Quantification of B-Trace Protein*", Clinical Chemistry at http://www.clinchem.org/cgi/content/full/60/12/2401; vol. 50, pp. 2401-2403 (2004).

Bachmann, et al; "Beta-trace-Protein in der Diagnostik der Liquorfistel"; HNO, vol. 48, No. 7, pp. 496-500 (2000). This article discloses the following: Beta-trace protein is a lipocalin that was recently identified as prostaglandin D synthase and represents a major constituent of human cerebrospinal fluid. Beta-trace protein, similar to beta 2-transferrin, has been used as an immunological marker for the detection of cerebrospinal fluid. Between 1982 and 1999, 130 specimens from 101 patients with suspected cerebrospinal fluid leaks of the anterior or lateral skull base.

Pentyala, et al.;"Cloning, Recombinant Expression and Purification of Prostaglandin D2 Synthase, a CSF Marker Protein: Implications in Safe Epidural Anesthesia"; Abstract of paper presented at the International Anesthesiology Research Society Meeting, Mar. 2005, Honolulu, USA, 2 pages.

Melegos, et al.; "Immunofluorometric Assay of Prostaglandin D Synthase in Human Tissue Extracts and Fluids"; Clinical Chemistry; 42; pp. 1984-1991; (1996).

Merriam-Webster Online Dictionary, definition of the term "In situ", retrieved from www.m-w.com.

International Search Report and Written Opinion; International Application No. PCT/US07/16907; International Filing Date Jul. 27, 2007; Applicant's File Reference 102888A-201; Date of Mailing Mar. 10, 2008; 14 pages.

Supplementary European Search Report; International Application No. PCT/US04/10635; International Filing Date Apr. 7, 2004; Date of Mailing Nov. 2, 2004; 1 page.

Harlow et al; "Monoclonal Antibodies"; Antibodies: A Laboratory Manual; Cold Spring Harbor Lab Press; pp. 141-142, 175; (1988).

Information Hyperlinked Over Proteins; Entry for PTGDS, Retrieved From http://www.Ihop-Net.Org/Unipub/Ihop?Gs/91453.Html; Aug. 8, 2007.

Anesthesiology News; "New Device Finds CSF Leaks in Minutes"; 33:05; McMahon Publishing Group, 2 pages; 2007.

Pentyala; "Design, Assembly and Validation of Lateral Flow Device Using Gold Nanoparticles: Development of CSF Leak Diagnostic Kit"; International Conference on Nanotechnology; Bangalore, India; Aug. 2006; Abstract Only; one page.

Pentyala; "Development of Lateral Flow Diagnostic Device for Rapid Detection of Cerebrospinal Fluid Leaks"; 81st IARS, Orlando, Florida; Mar. 2007; AUA, Chicago IL; Apr. 2007; Abstract Only; one page.

Pentyala; "Rapid Diagnostic in Critical Care: Nanobeads in Lateral Flow Technology"; Conference on Nanobiotechnology; Pune, India; Aug. 2006; Abstract Only; one page.

Pentyala; "Lateral Flow Device for the Detection of Cerebrospinal Fluid Leaks"; World Nanobiotech Congress; Boston, NY, Nov. 2007; Abstract Only; one page.

Harlow; Antibodies: A Laboratory Manual; Cold Spring Harbor Laboratory Press; Cold Spring Harbor, NY; pp. 54-61, 72-74, 124, 153, 173-174, and 474-478; (1988).

Creighton, et al.; "Proteins: Structures and Molecular Properties"; Second Edition, W.H. Freeman and Company, New York; pp. 353-354; (1993).

Janeway et al.; Immunobiology: the Immune System in Health and Disease; Elservier Science Ltd/Garland Publishing, New York, NY, Fourth Edition, pp. 34-40; (1999).

Merriam-Webster Online Dictionary, definitions for the terms "absorb", "adsorb", "Absorbent", "Adsorbent", and "Adsorption"; (2009). Retrieved Apr. 30, 2009, from http://www.Merriam-webster.com.

Oda, et al.; "Development and Evaluation of a Practical ELISA for Human Urinary Lipocalin-Type Prostaglandin D Synthase"; Clinical Chemistry; 48:9; pp. 1445-1453; (2002).

International Search Report and Written Opinion; International Application No. PCT/US2009/040343; International Filing Date: Apr. 13, 2009; Applicant's File Reference: AFI0001PCTP2; Date of Mailing: Nov. 30, 2009; 13 pages.

\* cited by examiner

METHOD AND KITS FOR DETECTING CEREBROSPINAL FLUID IN A SAMPLE

CROSS-REFERENCE TO RELATED APPLICATIONS

This application is a Divisional of U.S. Ser No. 11/516,385, filed Sep. 6, 2006, which is a Continuation-in-Part Application of U.S. Ser. No. 10/409,758 filed Apr. 9, 2003, now abandoned, which is incorporated by reference herein in its entirety.

BACKGROUND OF THE INVENTION

1. Field of the Invention

The present invention relates to detection of the presence or absence of cerebrospinal fluid (CSF) in a sample, in particular to the analysis of the CSF protein lipocalin-type prostaglandin D2 synthase (L-PGDS). The present invention provides assays for the analysis of L-PGDS indicating the presence or absence of CSF in a sample.

2. Brief Description of the Related Art

Neural blockade is associated with many complications. Among the most feared is accidental, unrecognized penetration of nervous system compartments containing cerebrospinal fluid (CSF). If puncture into the CSF is not noted immediately, or if it is incorrectly diagnosed, subsequent drug administration may lead to paralysis or death. Despite widespread use during surgery, childbirth and pain relief, current methods to detect CSF during and after neural blockade are unreliable, costly and time-consuming.

Patients undergoing epidural anesthesia and analgesia are at particular risk for needle puncture into the CSF. The epidural space is identified prior to blockade by loss of resistance to syringe injection of air, or of water solutions containing salt or sugar. Placement of the needle in the epidural space is followed by injection of drugs dissolved in sugar- or salt-containing water solutions in serial increments. If the epidural blockade is to be maintained for a long interval, a catheter may be threaded through the needle for both continuous and intermittent injection of drug-containing solutions. Because penetration of the dura and unintended entry into the CSF is possible at any step, the needle and catheter are routinely observed for passive drainage of CSF, and aspirated for fluid return before each manipulation and drug administration. If CSF is present, repositioning of the needle or catheter may be required to avoid spinal rather than epidural blockade upon drug injection.

Although unambiguous identification of drained or aspirated CSF is essential for the safe conduct of epidural anesthesia, caregivers are often uncertain over the origin of fluid that may be present. CSF is clear and watery, thereby closely resembling injected sugar- or salt-containing solutions and drug mixtures. In the past, efforts to discriminate CSF from injected or accumulated fluids have relied on physical properties such as temperature, or in vitro precipitation with second compounds, or on measurement of the possible chemical constituents of the fluid in question, such as glucose, protein, or ion levels. However, because of sample admixture, variability in test precision and inconsistent test thresholds, these methods are rarely helpful and little used.

At present, measurement of beta-2 transferrin in a sample is the only laboratory test to reach clinical practice capable of unequivocal discrimination of CSF, but its use is hampered in many regards. Each sample must be provided in high volume requiring as much as 1-2 mL of sample/assay. Turn-around time for results to reach the caregiver takes up to 4 days. Because immunofixation electrophoresis is necessary to detect beta-2 transferrin, the assay is expensive ($230-300/sample), and carries multiple added costs for specimen handling, archiving, shipping and storage. Moreover, special technical skills and experienced technicians are required to assure test precision and reliability, mandating that beta-2 transferrin assays be performed by specialty laboratories.

Clearly there is a great need for a rapid, robust, cost effective and accurate method to unambiguously identify CSF in samples obtained at the bedside during and after neural blockade. The present invention is believed to be an answer to that need.

SUMMARY OF THE INVENTION

The present invention relates to detection of the presence or absence of cerebrospinal fluid in a sample, in particular to the analysis of the CSF protein lipocalin-type prostaglandin D2 synthase (L-PGDS). The present invention provides assays for the analysis of L-PGDS indicating the presence or absence of CSF in a sample.

Accordingly, in some embodiments, the present invention provides a method for the detection of cerebrospinal fluid in a sample, comprising providing a sample from a subject, and detecting the presence or absence of lipocalin-type prostaglandin D2 synthase in said sample. In some embodiments, one or more additional compounds are detected, alone or in combination with, lipocalin-type prostaglandin D2 synthase. In some embodiments, beta-2 transferrin is detected. In some embodiments the subject has spontaneous otorrhea or rhinorrhea. In other embodiments, the subject has undergone trauma. In further embodiments, the subject has undergone surgery. In preferred embodiments, the subject is undergoing, or has undergone, neural blockade.

The present invention also provides a method wherein the amount of lipocalin-type prostaglandin D2 synthase is correlated to a known value to determine the presence or absence of cerebrospinal fluid in the sample. In preferred embodiments the presence or absence of cerebrospinal fluid in a sample comprises determining the amount of lipocalin-type prostaglandin D2 synthase in the sample. In some embodiments lipocalin-type prostaglandin D2 synthase is present at a concentration of less than approximately 2.0 mg/L. In other embodiments, lipocalin-type prostaglandin D2 synthase is present at concentration of between approximately 2.0 mg/L and approximately 6.0 mg/L. In yet other embodiments, lipocalin-type prostaglandin D2 synthase is present at a concentration of between approximately 6.0 and approximately 10.0 mg/L. In still other embodiments, lipocalin-type prostaglandin D2 synthase is present at a concentration of greater than approximately 10.0 mg/L The present invention also provides a method of determining the presence or absence of cerebrospinal fluid in a sample comprising determining the ratio of lipocalin-type prostaglandin D2 synthase in the serum, to lipocalin-type prostaglandin D2 synthase in a sample. In some embodiments the ratio is less than 10. In other embodiments, the ratio is between 10 and 20. In still other embodiments, the ratio is greater than 20.

The present invention further provides a method for detection of cerebrospinal fluid in a sample when the sample is obtained from a superficial opening on the body. In other embodiments, the sample is obtained from a needle in the body. In still other embodiments, the sample is free flowing. In yet other embodiments, the sample is aspirated. In further embodiments, the sample is obtained from a catheter. In additional embodiments, the sample is free flowing from the catheter. In further embodiments, the sample is aspirated from a catheter. In additional embodiments, the sample is obtained at serial intervals for the duration the catheter is in place. In preferred embodiments, the sample is obtained before catheter placement. In particularly preferred embodiments, the sample is obtained after catheter placement.

In some embodiments, the sample is obtained before administration of fluid. In other embodiments, the sample is obtained after administration of fluid. In preferred embodiments, the sample is obtained before administration of a drug. In particularly preferred embodiments, the sample is obtained after administration of a drug.

In some embodiments, the subject is a mammal. In other embodiments, the subject is a human. In further embodiments, the subject is undergoing surgery. In still further embodiments, the subject is undergoing acute pain management. In preferred embodiments, the subject is undergoing pain management after surgery. In other embodiments the subject is undergoing pain management after trauma. In particularly preferred embodiments, the subject is undergoing pain management during labor and delivery. In some embodiments, the subject is undergoing chronic pain management. In further embodiments, the pain comprises malignant pain. In still further embodiments, the pain comprises non-malignant pain.

The present invention also provides a method for detecting the presence or absence of cerebrospinal fluid in a sample from a subject undergoing neural blockade when the neural blockade comprises regional analgesia. In some embodiments, the regional analgesia comprises spinal analgesia. In some embodiments, the spinal analgesia comprises a single drug dose. In other embodiments, the spinal analgesia is continuous through a catheter. In preferred embodiments, the regional analgesia comprises epidural analgesia. In some embodiments, the epidural analgesia comprises a single drug dose. In other embodiments, the epidural analgesia is continuous through a catheter. In additional embodiments, the regional analgesia is combined spinal and epidural analgesia. In other embodiments, the regional analgesia comprises a peripheral nerve block. In still other embodiments, the regional analgesia comprises a plexus neural blockade. In further embodiments, the regional analgesia comprises an implanted drug delivery system. In still further embodiments, the regional analgesia comprises a nerve stimulator.

The present invention provides a method for the detection of cerebrospinal fluid in a sample, comprising providing a sample from a subject, and detecting the presence or absence of lipocalin-type prostaglandin D2 synthase in said sample using any suitable method. In some embodiments, detection comprises differential antibody binding. In a preferred embodiment, detection comprises an in situ immunoassay. In a particularly preferred embodiment, detection comprises an in situ immunoassay using a colloidal gold label. In other embodiments, differential antibody binding comprises a Western blot. In still other embodiments, differential antibody binding comprises a nephelometric assay. In further embodiments, the presence or absence of lipocalin-type prostaglandin D2 synthase in a sample is detected by a chromatographic assay. In other embodiments, the presence or absence of lipocalin-type prostaglandin D2 synthase in a sample is detected by an enzymatic assay. In still other embodiments, the presence or absence of lipocalin-type prostaglandin D2 synthase in a sample is detected by a spectroscopic assay.

The present invention further provides a kit comprising a reagent for detecting the presence or absence of lipocalin-type prostaglandin D2 synthase in a sample before, during, or after neural blockade. In some embodiments, the kit further comprises instructions for using the kit for detecting the presence or absence of lipocalin-type prostaglandin D2 synthase in a sample. In some embodiments, the instructions comprise instructions required by the U.S. Food and Drug Administration for in vitro diagnostic kits. In some embodiments, the kit further comprises instructions for diagnosing the presence or absence of cerebrospinal fluid in a sample based on the presence or absence of lipocalin-type prostaglandin D2 synthase in said sample. In some embodiments, the reagent comprises one or more antibodies. In other embodiments, the reagent comprises one or more enzymes, enzyme inhibitors or enzyme activators. In still other embodiments, the reagent comprises one or more chromatographic compounds. In yet other embodiments, the reagent comprises one or more compounds used to prepare the sample for spectroscopic assay. In further embodiments, the kit comprises comparative reference material to interpret the presence or absence of lipocalin-type prostaglandin D2 synthase according to intensity, color spectrum, or other physical attribute of an indicator.

Therefore, in one aspect, the present invention is directed to a method for detecting the presence or absence of cerebrospinal fluid in a sample, comprising the steps of: (1) providing a sample from a subject; (2) analyzing the sample for the presence or absence of lipocalin-type prostaglandin D2 synthase; and (3) correlating the presence or absence of the lipocalin-type prostaglandin D2 synthase with the the presence or absence of the cerebrospinal fluid in the sample.

In another aspect, the present invention is directed to a device for detecting the presence or absence of cerebrospinal fluid in a sample, comprising: an absorbant membrane comprising a sample zone comprising a first monoclonal antibody to lipocalin-type prostaglandin D2 synthase; a test zone comprising a second monoclonal or polyclonal antibody to lipocalin-type prostaglandin D2 synthase immobilized to the membrane; and a control zone comprising an immobilized rabbit anti-mouse antibody.

BRIEF DESCRIPTION OF THE FIGURES

FIG. 2 shows antibody-mediated detection of PGDS in CSF and other body fluids.

DETAILED DESCRIPTION OF THE INVENTION

CSF is a clear liquid similar in appearance to water, and in composition to plasma. The brain and spinal cord are rendered buoyant and protected by the CSF. Clinical, surgical and accidental events may cause CSF to breach its physiologic barriers. CSF leaks may occur with the placement of needles and catheters for anesthesia and analgesia, trauma, skull fractures, intracranial surgical procedures, infection, hydrocephalus, congenital malformations, neoplasms, and spontaneous rhinorrhea, and otorrhea.

Figure 1:
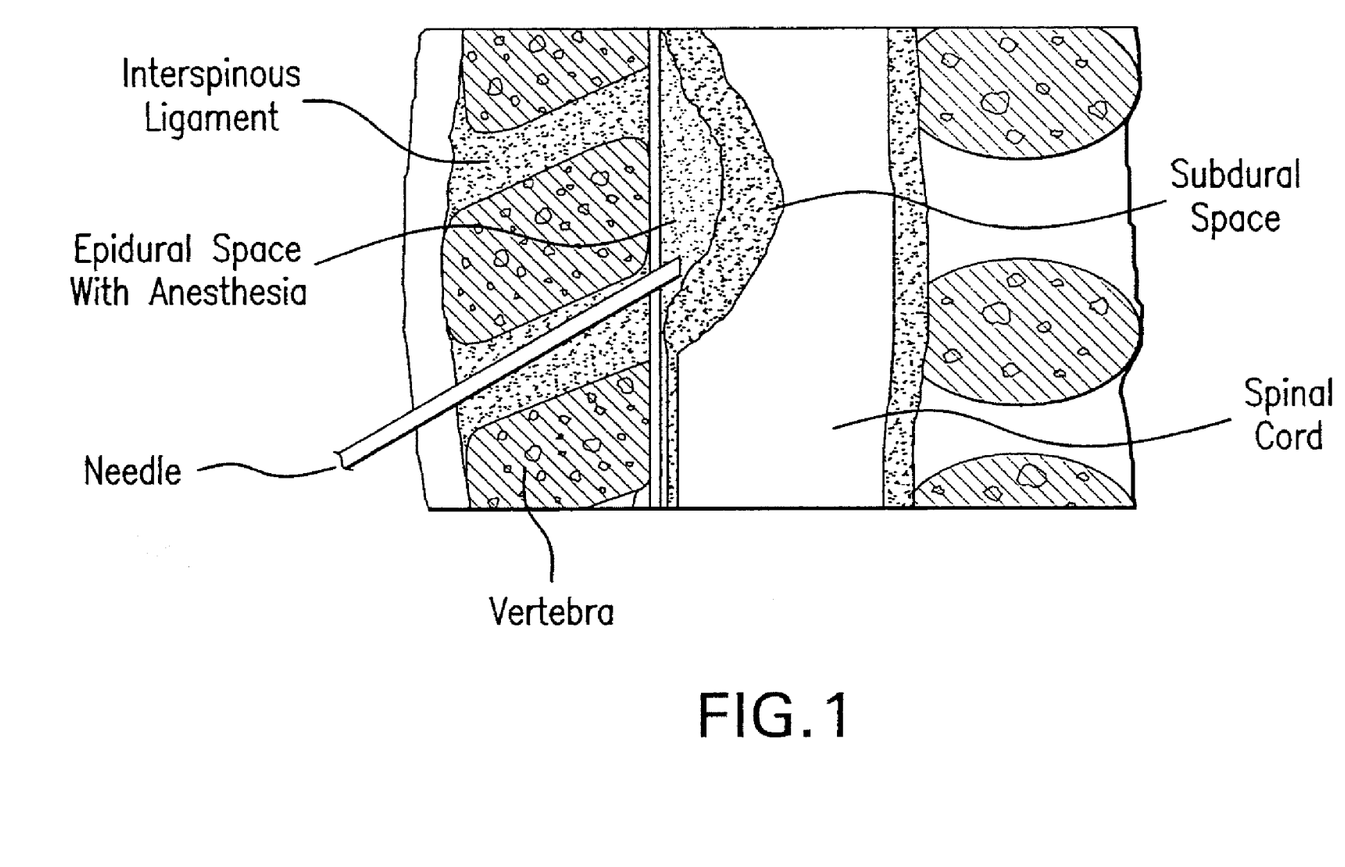
FIG. 1 shows spinal anatomy and placement of a needle tip within the epidural space. CSF surrounds and cushions the spinal cord and conus medullaris. Presence of CSF in catheter or needle drainage or aspirate indicates penetration of the dural membrane. Identical drugs and dosages administered into the epidural and spinal compartments have widely divergent kinetics (e.g. time to onset, duration of effects), and physiologic consequences (e.g. extent of motor, sensory and autonomic blockade) because of differential distribution of the pharmacologically active agents.

The risk of dural puncture and entry into the CSF is particularly high in epidural anesthesia and analgesia. Epidural opioids and local anesthetics are most commonly injected in the lumbar or thoracic region. The needle for epidural neural blockade passes between the vertebrae of the spinal column into the epidural space. The epidural space is normally devoid of fluids, and the distance across it is small (FIG. 1). If the epidural needle is advanced too far, it will pierce the dura which contains the spinal cord, spinal nerves and CSF. A hole in the dura may allow CSF to leak into the epidural space causing severe headaches. In patients with increased intracranial pressure, accidental dural puncture made while locating the epidural space risks cerebellar or tentorial herniation due to loss of CSF. Other serious complications include permanent paralysis, cardiac arrest and death.

Spinal block arising from undesired drug administration into the CSF is of major concern to anesthesiologists. This may occur if the medication intended for the epidural space is mistakenly administered into the spinal fluid, causing sudden and profound hypotension, lower extremity paralysis, impaired ventilation and cardiac rhythm disorders. To prevent and diagnose these conditions, the anesthesiologist carefully evaluates and monitors the patient's reaction to test doses of the anesthetic or analgesic drugs. However, at present there is no rapid and reliable method to evaluate the incidence of dural puncture and CSF leakage during procedures such as these, which are performed by the thousands every day.

The optimal method to detect dural puncture is to test for the presence or absence of CSF. Chemical analysis of fluid for glucose, protein, potassium or sodium is unreliable as a means of determining if the fluid is CSF. Radiographic studies are only intermittently successful in demonstrating small or delayed CSF leaks, are cumbersome, costly, time consuming, and carry risks of exposure to radiation and to radioisotopic dyes. Electrophoresis of fluid from a suspected CSF source combined with immunofixation to detect the CSF protein constituent beta-2 transferrin has been shown to be a specific and generally accepted method of detecting CSF. However, the beta-2 transferrin assay requires the coordination of multiple acquisition and handling steps, is prohibitively time consuming for use during and after neural blockade (4 days), and is expensive ($300/assay).

Lipocalin-type prostaglandin D2 synthase (L-PGDS), also referred to as the beta-trace protein, is secreted into the CSF after production in the choroid plexus, leptomeninges, and oligodendrocytes of the central nervous system. L-PGDS catalyzes the isomerization of prostaglandin H2 to prostaglandin D2 (PGD), which serves as an endogenous sleep-promoting compound. In comparison to transferrin, for which only the beta-2 isoform is specific to CSF, the entire structure of PGDS is specific to CSF. L-PGDS is therefore preferred for use in the present invention as a rapid and specific indicator of the presence or absence of CSF.

Experiments conducted during the course of development of the present invention demonstrate that L-PGDS is a reliable marker for CSF, and is less expensive and less time-consuming than conventional methods. The present invention provides novel methods and kits for rapid detection of CSF in samples obtained before, during and after neural blockade. Use of the present invention assures safer performance of neural blockade, and reduces the incidence and severity of life-threatening complications.

Definitions

To facilitate understanding of the invention, a number of terms are defined below.

As used herein, the term "subject" encompasses humans and animals, whether or not hospitalized.

As used herein, the term "L-PGDS" or "lipocalin-type prostaglandin D2 synthase" is used in reference to a specific protein which is secreted into the CSF after production in the choroid plexus, leptomeninges, and oligodendrocytes of the central nervous system, which catalyzes the isomerization of prostaglandin H2 to prostaglandin D2, and which is correlated with the presence or absence of CSF. The above definition of L-PGDS serves to distinguish this protein from hematopoetic type PGDS.

As used herein, "neural blockade" refers to administration of cellular receptor agonists and antagonists in direct proximity to targeted neuronal structures for the purposes of interfering with neuronal transmission. Neural blockade includes, but is not limited to, regional anesthesia (e.g. spinal, epidural, peripheral or plexus anesthesia), and regional analgesia (e.g. spinal, epidural, peripheral or plexus analgesia).

As used herein, the term "is undergoing" is used in reference to being subjected to neural blockade.

As used herein, the term "malignant pain" refers to pain arising from a cancerous or neoplastic origin including pressure, ischemia, necrosis, obstruction and other consequences of tumor location and growth.

As used herein, the term "non-malignant pain" refers to pain arising from causes other than cancer.

As used herein, the term "regional analgesia" is used in reference to neural blockade to refer to agents and procedures used to reduce or eliminate pain in a region of the body without direct interference with consciousness.

As used herein, the term "continuous" is used in reference to neural blockade wherein drugs are infused through a catheter to the desired site of action without interruption.

As used herein, the term "spinal" is used in reference to neural blockade to refer to administration of a drug or drugs beneath the dura and into the cerebrospinal fluid.

As used herein, the term "epidural" is used in reference to neural blockade to refer to administration of a drug or drugs within the epidural space external to the dural membrane of the nervous system.

As used herein, the term "peripheral" is used in reference to neural blockade to refer to administration of a drug or drugs directly in proximity to a peripheral nerve external to the central nervous system.

As used herein, the term "plexus" is used in reference to neural blockade to refer to administration of a drug or drugs directly in proximity to a nerve plexus external to the central nervous system.

As used herein, the term "implanted drug delivery system" is used to refer to a device indwelling in the body capable of providing a drug or drugs to the nervous system (e.g. through a catheter) either as a continuous infusion or in response to patient demand.

As used herein, the term "nerve stimulator" is used in reference to a device indwelling in the body capable of providing constant or intermittent electrical current or voltage in relief of malignant and non-malignant pain.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

The terms "fragment" or "portion" as used herein refer to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

As used herein, the term "purified" or "to purify" refers to the removal of contaminants from a sample. For example, PGDS antibodies are purified by removal of contaminating non-immunoglobulin proteins; they are also purified by the removal of immunoglobulin that does not bind PGDS. The removal of non-immunoglobulin proteins and/or the removal of immunoglobulins that do not bind PGDS results in an increase in the percent of PGDS-reactive immunoglobulins in the sample. In another example, recombinant PGDS polypeptides are expressed in bacterial host cells and the polypeptides are purified by the removal of host cell proteins; the percent of recombinant PGDS polypeptides is thereby increased in the sample. The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

As used herein, the term "nephelometric assay" is used to refer to an assay developed by Dade Behring (Liederbach, Germany), consisting or polystryene particles coated with immunoaffinity-purified polyclonal antibodies from rabbit against human PGDS. The increase in light scattering caused by agglutination is measured by laser absorption.

The term "sample" as used herein is used in its broadest sense. A sample suspected of containing a protein may comprise a cell or can be cell-free, a portion of a tissue, an extract containing one or more proteins, body fluid, and the like. A "free flowing" sample refers to passive drainage of body fluid from a needle, catheter or other instrument penetrating a body compartment.

As used herein, the term "response", when used in reference to an assay, refers to the generation of a detectable signal (e.g., accumulation of reporter protein, increase in ion concentration, and accumulation of a detectable chemical product).

As used herein, the term "instructions for using said kit for said detecting the presence or absence of PGDS polypeptide in a said biological sample" includes instructions for using the reagents contained in the kit for the detection of PGDS polypeptides. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

As used herein, the term "superficial opening" refers to a natural or acquired aperture on the surface of the body.

As indicated above, the present invention is directed to a method for detecting the presence or absence of cerebrospinal fluid in a sample, comprising the steps of: (1) providing a sample from a subject; (2) analyzing the sample for the presence or absence of lipocalin-type prostaglandin D2 synthase (L-PGDS); and (3) correlating the presence or absence of the lipocalin-type prostaglandin D2 synthase with the the presence or absence of the cerebrospinal fluid in the sample. Each of these steps is explained in more detail below.

As indicated above, the sample provided in the method of the present invention is defined in its broadest sense and includes cellular or cell free extracts, a portion of a tissue, an extract containing one or more proteins, body fluid, and the like. The sample may be obtained from subjects by passive drainage of body fluid from a needle, catheter or other instrument penetrating a body compartment.

Detection of L-PGDS Protein

As described above, a new method of detecting or analyzing for the presence or absence of CSF has been developed. Accordingly, the present invention provides methods for detecting L-PGDS in a sample from a subject, including subjects undergoing or having undergone neural blockade. Any suitable method may be used to detect or analyze for L-PGDS polypeptides. For example, in some embodiments a chromatographic method wherein the presence of L-PGDS produces a detectable color change is utilized. In other embodiments an enzymatic method wherein the presence of L-PGDS initiates detectable enzymatic activation is utilized. In further embodiments the presence of L-PGDS in a sample is detected by atomic absorption or atomic emission spectroscopy.

In certain embodiments of the present invention, the L-PGDS protein (also referred to as "prostaglandin-H2 D-isomerase", and "beta-trace protein") is a glycoprotein with a molecular mass of about 26 kDa (EC 5.3.99.2) belonging to the lipocalin family of secretory proteins. In preferred embodiments the L-PGDS protein catalyzes the isomerization of $PGH_2$ to produce $PGD_2$. In further embodiments the cDNA of human PGDS encodes 190 amino acid residues with an N-terminal signal peptide of 22 amino acid residues. In particularly preferred embodiments, the PGDS protein is the "brain-type" isoform with brain-specific N-glycosylation oligosaccharide chains.

In a preferred embodiment of the present invention, antibodies are used to determine if a sample contains L-PGDS indicating the presence or absence of CSF (see Generation of L-PGDS Antibodies below). Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a score correlating to the presence of PGDS and likelihood of CSF in a sample based on the result of the immunoassay is utilized.

In other embodiments, the immunoassay is as described in U.S. Pat. Nos. 5,599,677 and 5,672,480, each of which is herein incorporated by reference.

Generation of L-PGDS Antibodies

The present invention provides isolated antibodies or antibody fragments (e.g., Fab fragments, $Fab_2$ fragments, and the like). Antibodies can be generated to allow for the detection of PGDS protein. The antibodies may be prepared using various immunogens. In one embodiment, the immunogen is a human L-PGDS peptide to generate antibodies that recognize human L-PGDS. Such antibodies include, but are not limited to polyclonal, monoclonal, chimeric, single chain, Fab fragments, Fab expression libraries, or recombinant (e.g., chimeric, humanized, etc.) antibodies, as long as it can recognize the protein. Antibodies can be produced by using a protein of the present invention as the antigen according to a conventional antibody or antiserum preparation process.

Various procedures known in the art may be used for the production of polyclonal antibodies directed against PGDS. For the production of antibody, various host animals can be immunized by injection with the peptide corresponding to the L-PGDS epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward L-PGDS, it is contemplated that any technique that provides for the production of antibody molecules by continuous cell lines in culture will find use with the present invention (See e.g., Harlow and Lane, Antibodies: A Laboratory Manual, Cold Spring Harbor Laboratory Press, Cold Spring Harbor, N.Y.). These include but are not limited to the hybridoma technique originally developed by Kohler and Milstein (Kohler and Milstein, Nature 256:495-497, 1975), as well as the trioma technique, the human B-cell hybridoma technique (See e.g., Kozbor et al., Immunol. Tod., 4:72, 1983), and the EBV-hybridoma technique to produce human monoclonal antibodies (Cole et al., in Monoclonal Antibodies and Cancer Therapy, Alan R. Liss, Inc., pp. 77-96, 1985).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026-2030 [1983]) or by transforming human B cells with EBV virus in vitro (Cole et al., in Monoclonal Antibodies and Cancer Therapy, Alan R. Liss, pp. 77-96 [1985]).

In addition, it is contemplated that techniques described for the production of single chain antibodies (U.S. Pat. No. 4,946,778; herein incorporated by reference) will find use in producing L-PGDS specific single chain antibodies. An additional embodiment of the invention utilizes the techniques described for the construction of Fab expression libraries (Huse et al., Science 246:1275-1281, 1989) to allow rapid and easy identification of monoclonal Fab fragments with the desired specificity for L-PGDS.

In other embodiments, the present invention contemplates recombinant antibodies or fragments thereof to L-PGDS. Recombinant antibodies include, but are not limited to, humanized and chimeric antibodies. Methods for generating recombinant antibodies are known in the art (See e.g., U.S. Pat. Nos. 6,180,370 and 6,277,969 and "Monoclonal Antibodies" H. Zola, BIOS Scientific Publishers Limited 2000. Springer-Verlay New York, Inc., New York; each of which is herein incorporated by reference).

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.).

The foregoing antibodies can be used in methods known in the art relating to the localization and structure of L-PGDS (e.g., for Western blotting), measuring levels thereof in appropriate biological samples, etc. The antibodies can be used to detect L-PGDS in a biological sample from an individual. The biological sample can be a biological fluid, such as, but not limited to, blood, serum, plasma, interstitial fluid, urine, cerebrospinal fluid, and the like.

The biological samples can then be tested directly for the presence of human PGDS using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of L-PGDS detected by immunoblotting (Western blotting). Immunoblotting techniques are generally more effective with antibodies generated against a peptide corresponding to an epitope of a protein, and hence, are particularly suited to the present invention.

The correlation step mentioned above may be implemented qualitatively or quantitatively, for example in a fluorophoric or colorimetric assay. In the method and device of the invention, since lipocalin-type prostaglandin D2 synthase is only found in cerebrospinal fluid, any indication of lipocalin-type prostaglandin D2 synthase in a sample can be directly correlated to the presence of cerebrospinal fluid in that sample.

Kits and Devices for Analyzing Presence or Absence of CSF

The present invention also provides kits and devices for determining whether a sample contains PGDS. The diagnostic kits and devices are produced in a variety of ways. In some embodiments, the kits and devices contain at least one reagent for specifically detecting an L-PGDS protein. In preferred embodiments, the kits and devices contain multiple reagents for detecting the L-PGDS protein. In particularly preferred embodiments, the reagents are antibodies that preferentially bind L-PGDS proteins.

In some embodiments, the kit or device contains instructions for determining whether the sample contains L-PGDS. In preferred embodiments, the instructions specify that presence or absence of CSF is determined by detecting the presence or absence of L-PGDS in a sample from the subject, wherein subjects are undergoing or have undergone neural blockade.

The presence or absence of an L-PGDS in a sample can be used to make therapeutic or other medical decisions. For example, deciding whether to use the existing catheter in place, or to replace the catheter during or after neural blockade, may be based on the presence or absence of L-PGDS-containing CSF in a sample obtained from the catheter.

In some embodiments, the kits and devices include ancillary reagents such as buffering agents, protein stabilizing reagents, and signal producing systems (e.g., fluorescence generating systems such as FRET systems). The test kit or device may be packaged in any suitable manner, typically with the elements in a single container or various containers as necessary, along with a sheet of instructions for carrying out the test. In some embodiments, the kits or devices also preferably include a positive control sample. In further embodiments, the kit or device contains comparative reference material to interpret the presence or absence of prostaglandin D2 synthase according to intensity, color spectrum, or other physical attribute of an indicator.

The need for a rapid, reproducible, sensitive and simple diagnostic test, which can be used in the health care for diagnosing CSF leaks, is of major importance. Such a test has the obvious advantage over the existing laboratory tests, i.e. immunofixation electrophoresis, enzyme-linked immunosorbent assay (ELISA) and immunoblotting, in that it can be performed immediately beside the patient giving a result in a few minutes of time instead of several days when the sample is sent for analysis to a laboratory. A lateral flow immunochromatographic test may be utilized for making a diagnostic kit for the detection of CSF in biological fluids.

Figure 4:
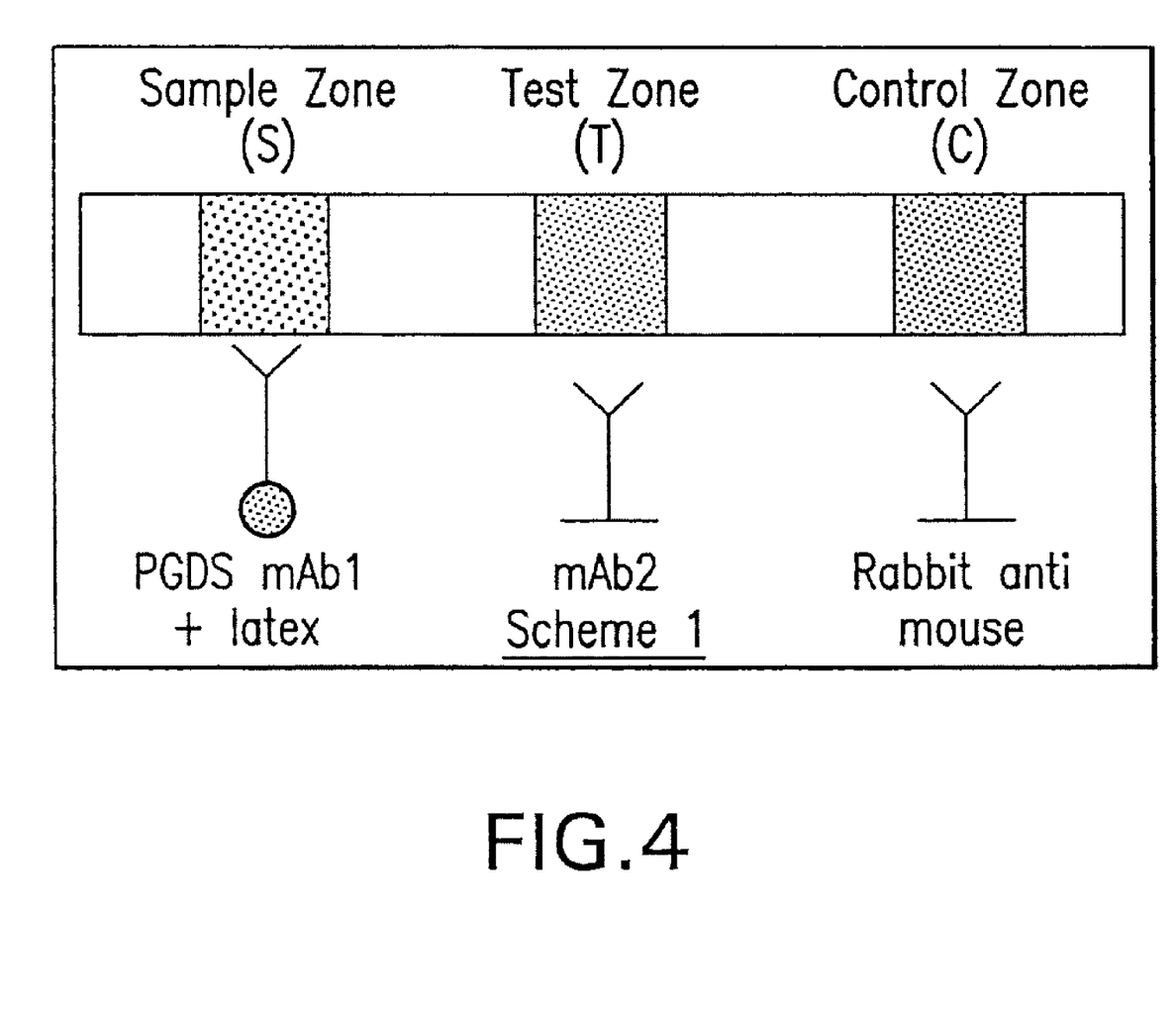
FIG. 4 depicts one embodiment of the device of the present invention.

The test device includes a test strip optionally with a plastic test cassette (FIG. 4). Antibodies are attached to three different zones on the membrane; a sample zone (S) containing a first monoclonal antibody to lipocalin-type prostaglandin D2 synthase; a test zone (T) that contains a second monoclonal or polyclonal antibody to lipocalin-type prostaglandin D2 synthase immobilized to the membrane; and a control zone (C), which contains, for example, an immobilized rabbit anti-mouse antibody. The first monoclonal antibody in the sample (S) zone may be conjugated to a mobile particle, for example, a colored latex particle or a gold particle. Alternatively, the first monoclonal antibody may be conjugated to a chromophoric indicator, such as a fluorescent molecule or tag (Green Fluorescent Protein (GFP), Alexa, Texas Red, and the like).

Figure 5A:
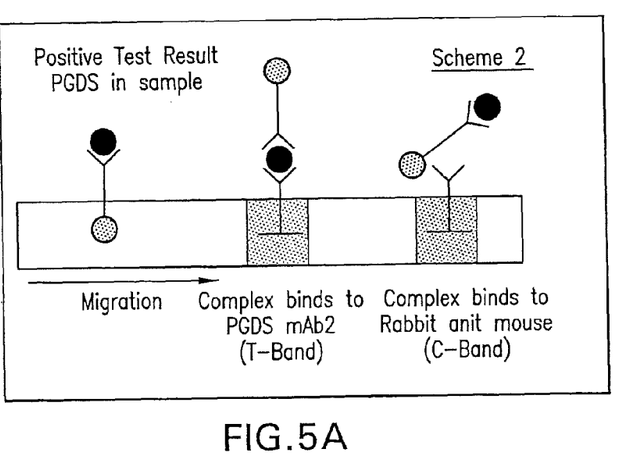
FIGS. 5A and 5B depict the mechanism of action of the device of the present invention.
Figure 5B:
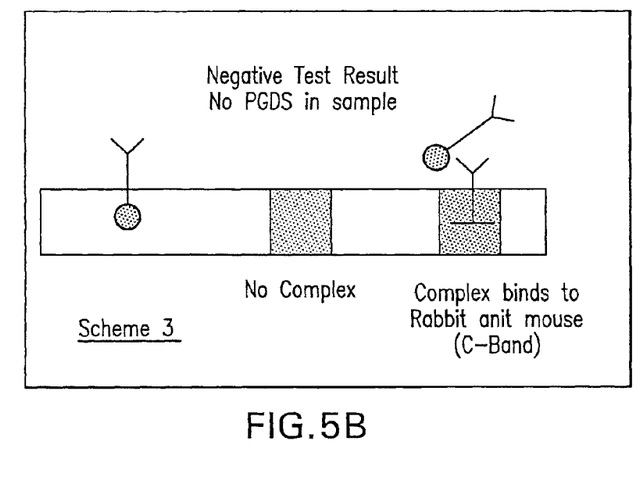

The device of the present invention is implemented utilizing an immunochromatographic test based on the use of two monoclonal antibodies. As shown in FIGS. 5A and 5B, sample is added to the S-zone, and if PGDS is present, it binds to the first monoclonal antibody to form a PGDS-conjugate-complex. This complex migrates chromatographically on the membrane, and when it reaches the immobilized antibody in the T-zone, agglutination takes place and a blue colored band is formed.

Briefly and in one embodiment, the first monoclonal antibody is conjugated to a mobile particle, for example, gold or latex beads. These beads have the intrinsic color of either being red (for gold) or can come in different colors if using latex beads. When the sample is applied on the "S-zone", the marker, L-PGDS if present in the sample, binds to the first monoclonal antibody that is conjugated to the beads and then because of the lateral flow absorbent pad on which the beads are placed, the complex (beads+antibody+PGDS if present in the sample) migrates laterally. Once the complex reaches the "T-zone" where the second antibody is immobilized on the strip, the marker that is now migrating with the complex binds to the second immobilized antibody. As the second antibody is stationary/fixed/immobilized, the whole complex gets trapped and as the complex now contains colored beads, the immobilized T-zone line lights up according to the beads that are used (red for gold or different colors {like blue} if latex beads are used). The excess complex sample migrates to the end of the strip and at the "C-zone" the first antibody conjugated to the beads is trapped by immobilized/fixed/stationary rabbit-anti mouse antibody and gives a colored line indicating that the test is complete). Thus, a colored band indicates a positive result (FIG. 5A). No band in the T-zone is significant for a negative result (FIG. 5B). The immobilized polyclonal antibody in the C-zone will bind the latex conjugate with both positive and negative samples. This blue band assures a correct test performance.

In practice, the kits and devices of the present invention can be utilized in a variety of clinical settings to determine the presence of CSF in a sample, including skull fractures, CSF leaks following various surgeries, such as endoscopic endonasal surgery, neurosurgery, epidural catheter placement, spontaneous intracranial hypotension, anthrax induced intracranial hypotension, or CSF leaks associated conditions such as rhinnorhea and otorrhea, hydrocephalus, intracranial neoplasms, congenital neural malformations, and the like.

EXAMPLES

The following examples and procedures are provided in order to demonstrate and further illustrate certain preferred embodiments and aspects of the present invention, and are not to be construed as limiting the scope thereof.

Methodology

Epidural eluates and CSF samples were obtained from patients in the labor and delivery unit of SUNY Stony Brook University Hospital. The body fluids were obtained from the Hematology and Chemistry labs of SUNY Stony Brook University Hospital. The samples were analyzed for PGDS with use of a polyclonal antibody specific for lipocalin PGDS (CAYMAN CHEMICAL CO. Ann Arbor Mich.).

Epidural Eluates

Following signed informed consent (IRB approved), and permission of the attending obstetrician, an epidural catheter was placed and dosed with routine epidural medications (3 cc of lidocaine-1.5% with epinephrine-1:200,000; and 10 cc of bupivacaine-0.125% with fentanyl-50 .mu.g). The patient was then placed on a continuous epidural infusion of bupivacaine 0.0625% with fentanyl 1.6 ug/cc at 10 cc/hr. For the purpose of this investigation, the epidural catheter was aspirated twice between one and four hours after the epidural placement. Aspirated fluid was tested for the presence of CSF by PGDS immunoblotting.

Spinal Fluid

Following signed informed consent (IRB approved), and permission of their obstetrician, patients having routine spinal anesthetic placement for elective cesarean section volunteered to donate a small volume of spinal fluid. After locating the subarachnoid space with 25 G pencan spinal needle, 1 mL of CSF was aspirated before injection of medications intended for anesthesia. Thus, CSF that is normally either discarded or injected back into the patient, was used to evaluate the presence of PGDS by immunoblotting.

Body Fluids

Other body fluids that were tested in this study were procured from the Clinical Laboratories of SUNY Brook University Hospital, Stony Brook, N.Y. After clinical analysis of the fluids as requested by the attending physician, these body fluid samples are routinely discarded. Rather than their destruction, with IRB approval these samples were taken up for evaluation of the presence of the CSF marker PGDS by immunoblotting.

Immunoblotting

Samples (5-20 ul) of CSF, and body fluids from other sources, were subjected to SDS-PAGE and electro-transferred to PVDF membranes. The membranes were blocked with 5% dry milk in TBS, and probed with anti-prostaglandin D2 synthase (anti-PGDS) antibody (CAYMAN CHEMICAL CO. Ann Arbor Mich.), followed by a secondary antibody labeled with HRP. The blots were then developed by enhanced chemiluminescence (ECL-Amersham).

Example 1

Figure 2A:
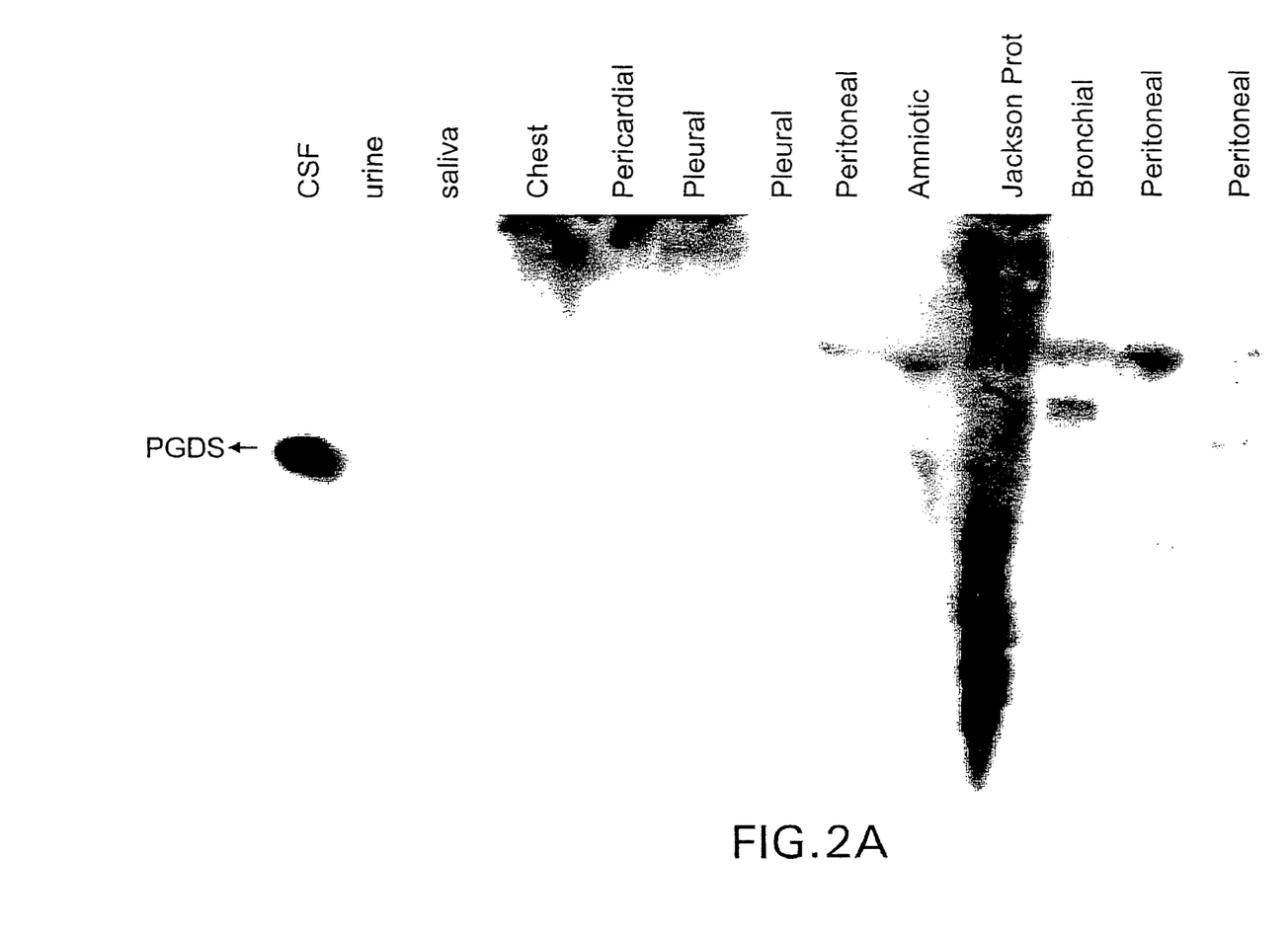
FIG. 2A shows specific binding of anti-PGDS antibody to PGDS from a CSF source, and absence of PGDS in samples from other sources.

Polyclonal anti-PGDS antibody reliably and specifically detects the presence of PGDS in CSF upon immunoblotting, and its absence in other body fluids (FIG. 2A). Sample volumes as small as 5 uL are suitable for accurate analysis.

Example 2

Figure 2B:
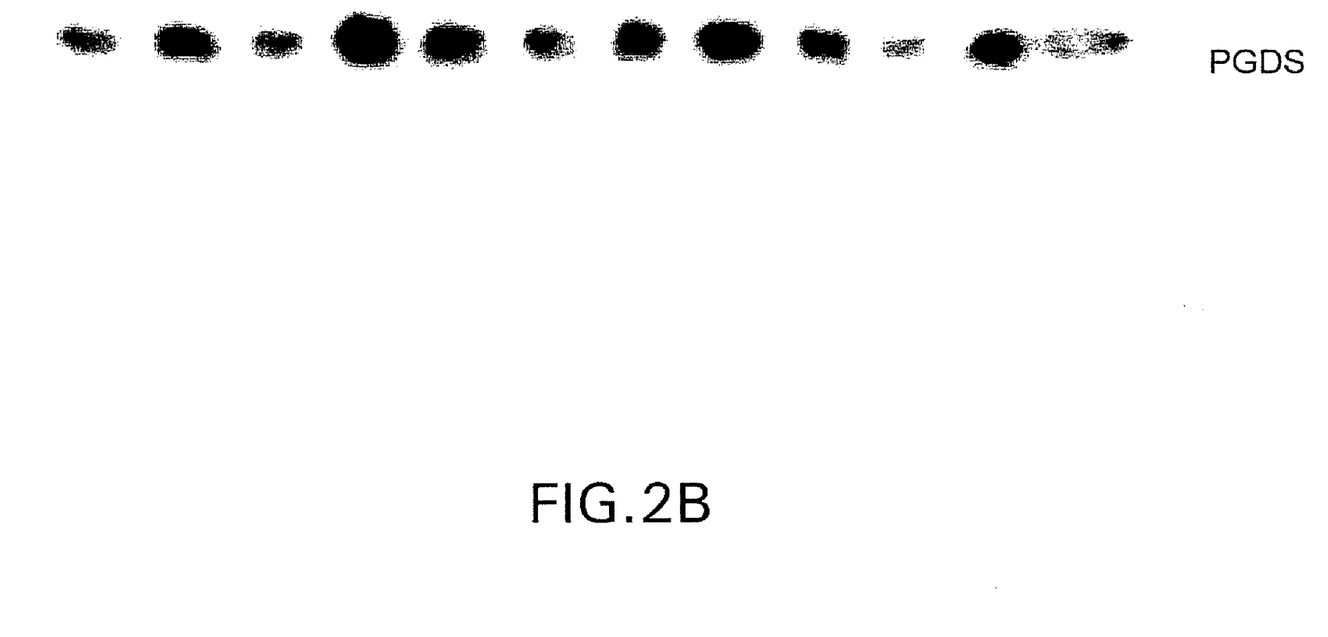
FIG. 2B shows anti-PGDS antibody detection of PGDS in samples of CSF from 12 distinct human sources.

Polyclonal anti-PGDS antibody reliably detects PGDS in CSF samples from 12 distinct human sources, indicating the antibody-mediated detection of PGDS in CSF is antigen-specific but not patient-specific (FIG. 2B).

Example 3

Figure 2C:
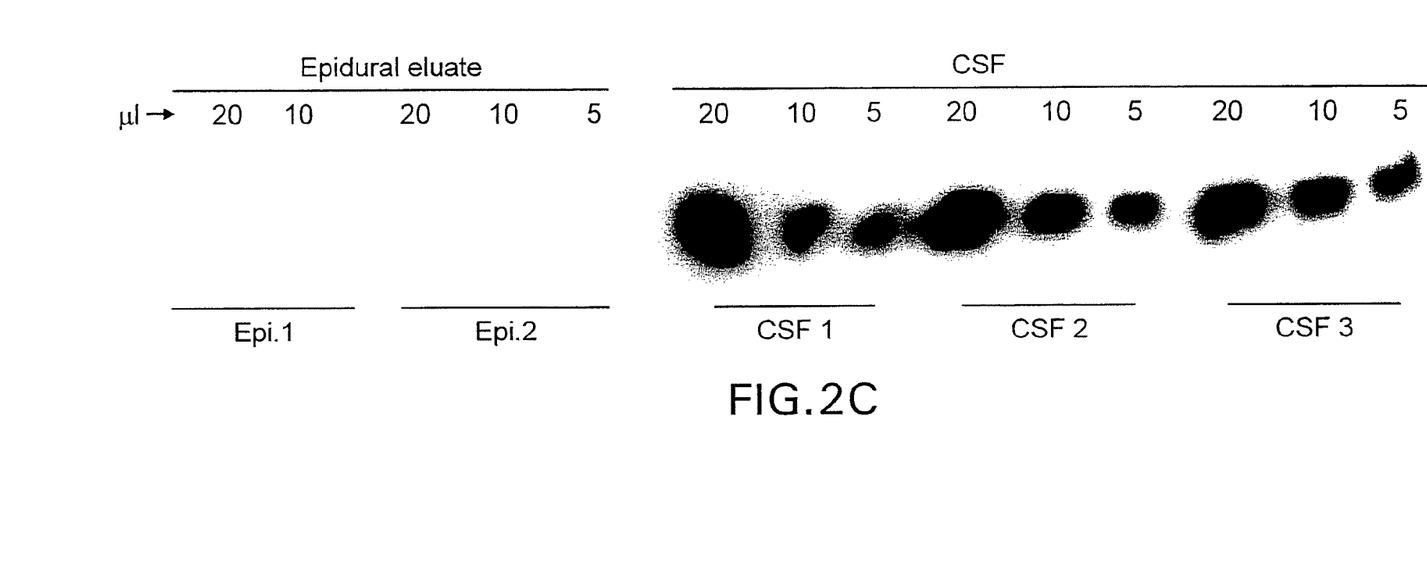
FIG. 2C shows absence of PGDS in epidural eluates, but presence of PGDS in CSF detected by anti-PGDS antibody binding in samples from 2 and 3 subjects, respectively.
Figure 3:
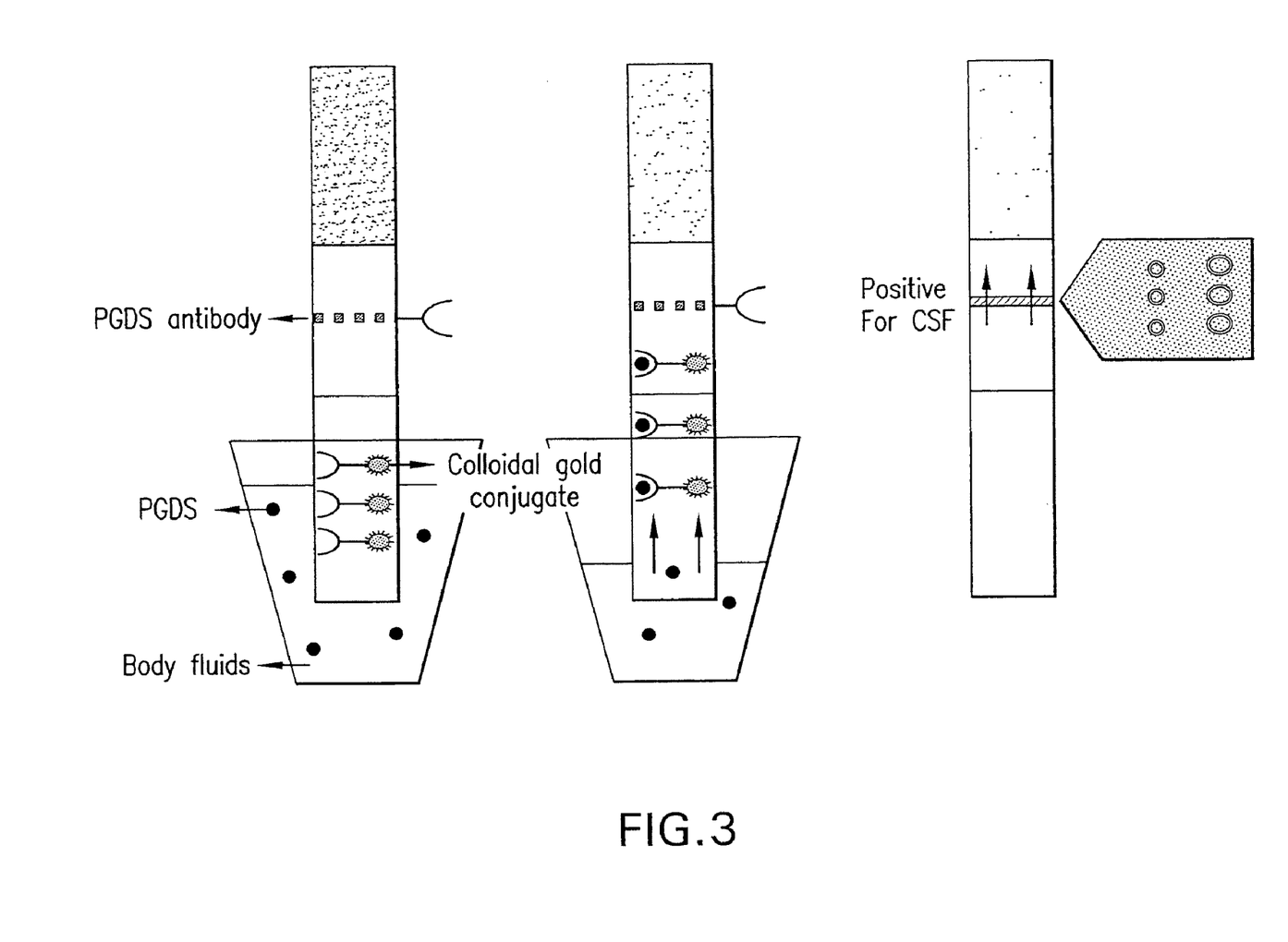
FIG. 3 shows bedside anti-PGDS in situ antibody-mediated detection of PGDS configured as an absorbent dipstick. Presence of a colloidal gold indicator band in the solid phase following immersion indicates presence of CSF in the test sample.

Polyclonal anti-PGDS antibody reliably discriminates aspirates of fluid from different body compartments. Strong anti-PGDS binding is observed in fluid samples from spinal sources, whereas no PGDS binding is seen in eluates from catheters in the epidural space (FIG. 2C).

These results indicate that the presence or absence of PGDS in body fluid samples reliably and specifically predicts the source of the fluid, and thereby discriminates between spinal, epidural and other body fluid compartment origins.

Example 4

Cloning of PGDS into a Bacterial Expression Vector

Plasmid pDNR-LIB (125-225 ng) containing the gene for PGDS was incubated with pLB-ProTet-6xHN acceptor vector (~200 ng) in a Cre Recombinase reaction (20 uL). Reactions were terminated and then used to transform competent DH5-alpha and BL21 bacterial cells, which were then plated on Luria Broth (LB) agar plates containing 30 ug/mL chloramphenicol and 7% sucrose. The gene of PGDS was also cloned into a pet15b vector with a His tag on the C-terminal end and was used to transform DH5-alpha and BL21 bacterial cells. Plasmid DNA was extracted from selected colonies, linearized by restriction enzyme, and run on an agarose gel.

Example 5

Purification of rPGDS by Affinity Chromatography

Cytosolic fraction of BL21 E.coli (transfected with Pro-Tet R or pet15b vector harboring PGDS gene) was extracted into Sigma Lytic II extraction buffer and the sample was applied to BD-TALON His-Arg affinity column or Nickel-NTA column and the bound rPGDS was eluted with imidazole. The samples were subjected to SDS-PAGE and immunoblotted with PGDS antibody.

Example 6

Generation of Monoclonal Antibodies

Monoclonal antibodies were generated against PGDS using a standard protocol (Lipsich et al, 1983). Three mice were immunized with PGDS peptide by four biweekly injections and sera was tested by ELISA. A mouse was chosen for fusion based upon having an antibody titer of 1:1000 against the antigen and boosted again with the antigen, followed by splenic fusion four days later. Isolated spleen cells were fused with mouse myeloma cell line SP2/O at a ratio of 10:1 spleen cells:myeloma cells by pelleting them together at 1000 rpm for 5 min in DMEM medium (Gibco) supplemented with 10% Fetal Clone I (HyClone), non-essential amino acids (Gibco) and penicillin and streptomycin (Gibco). The pellet was resuspended in 35% PEG 1500 (Roche) in DMEM medium, and the cells were immediately centrifuged at 1000 rpm for 5 min. The PEG was aspirated, and the fused cells were suspended in DMEM glutamax medium (Gibco) supplemented with 15% Fetal Clone I, 10% NCTC109 (Gibco), non-essential amino acids, penicillin and streptomycin, 10-4 M hypoxanthine, 4×10-7 M aminopterin, 1.6×10-5 M thymidine, and 10% macrophage conditioned medium and plated in ten 96 well plates. Macrophage conditioned medium was prepared as described (Rathejan et al, 1985) with modifications (Sugasawara et al, 1985). Briefly, J774.A1 (American Type Culture Collection) was cultured in a spinner flask in DMEM medium supplemented with 10% horse serum (Hy-Clone). Lipopolysaccharide (E. coli LPS 055:B5, Cal Biochem) was added to 5 ug/mL to the spinner culture, and the cells were incubated for 20 h. Cells were then harvested at 1000 rpm for 10 minutes and washed in one-half volume of PBS. Following centrifugation for 10 min at 1000 rpm, the supernatant was discarded and the cells resuspended in Iscoves modified Dulbecco's medium (IMDM, Gibco) without horse serum and transferred to a spinner flask. The cells were then incubated for 48 h at 37° C. The medium was harvested by pelleting the cells out of the medium by centrifugation at 1500 rpm for 10 min. The macrophage conditioned medium was then filtered and stored at 4° C. Two weeks following fusion, wells were screened by ELISA against PGDS peptide conjugated to ovalbumin. The day before screening, 0.1 mL of medium was removed from each well of the ten 96-well fusion plates and replaced with 0.1 mL per well of fresh medium. Wells exhibiting both a positive response by ELISA and cell growth were rescreened by ELISA the following day to confirm the response. Cells in wells exhibiting a positive response on retest were expanded and grown up to 30 mLs in culture and three 10-mL aliquots were pelleted and resuspended in freezing medium (10% dimethyl sulfoxide, 90% Fetal Clone I) for cryostorage. Positive samples were screened by dot blot against CSF and rPGDS, and clones were chosen for subcloning by limiting dilution. Subclones were screened by ELISA and subclones were chosen for further study, expanded and grown up to 1000 mL volume in DMEM supplemented with 10% fetal calf serum and antibiotics in T-175 flasks. Subclone was transferred to DMEM without serum and continued to incubate for three days. Supernatant was harvested by pelleting out the cells at 1500 rpm for 10 min and stored at 4° C.

Ten to fourteen days post fusion, clones were tested from 4000 wells by ELISA as an initial screen. Positive clones were retested by ELISA and in addition, were tested within two or three days by a second screen, such as dot blot. Recombinant PGDS was transferred to PVDF membrane using a dot blot apparatus and probed with ascites from hybridomas generated in the scheme of monoclonal antibody production.

Example 7

Detection of Native and Denatured PGDS in CSF

CSF (10 ul) was transferred to PVDF using a Bio-Rad dot blot apparatus (native protein) or electrophoresed and transferred to PVDF membrane (denatured protein) and probed with a PGDS antibody. The membrane was developed by using ECL detection Kit. The results indicate the detection of protein using L-PGDS specific antibody.

Example 8

Evaluating the Presence of PGDS in Samples Procured during Epidural Procedures and Identifying Wet-Taps due to CSF Leak Samples procured during epidural procedures by clinician collaborators after IRB approval, were evaluated for the presence of CSF marker (PGDS). The study was blinded until the samples were analyzed and later correlated with the designated samples. Designated spinal samples showed a strong presence of CSF marker where as designated epidural samples are free of marker.

Example 9

Scale-Up and Purification of Recombinant Protein and IgGs

Affinity chromatography techniques will be used for the purification recombinant protein and antibodies from selected subclones.

1. Large Scale Purification of rPGDS

E. coli BL-21PRO cells, transformed with expression vector, Pro-Tet6X-HN harboring the PGDSHN tagged gene or pet15b vector harboring His tagged PGDS gene are grown in Super broth. Induction of protein expression may be carried out at 20-23° C. by adding 8 ml of 100 mM anhydrotetracycline to an 800-ml bacterial culture when cell density ($A_{600}$) reached 0.6-0.7. Bacterial cells may be resuspended in binding buffer (20 mM Tris-HCl, pH 7.5, 100 mM NaCl, 10% glycerol, 1 mM phenylmethylsulfonyl fluoride, and 1 mM imidazole, pH 7.9) followed by sonication. Tagged recombinant L-PGDS is purified using TALON or Ni-NTA resin according to the manufacturer's protocol (BD Life Sciences, Franklin Lakes, N.J., or ClonTech, Mountain View, Calif.). After centrifugation (39,000× g), cell extract is incubated with 300 µl (bed volume) of TALON or Ni-NTA resin at 4° C. for 1-2 h. Beads are washed three times with 10 ml of washing buffer (same as binding buffer except with 10 mM imidazole). Proteins may be eluted with 300-500 µl of elution buffer (same as binding buffer except with 100 mM imidazole). Eluted samples are analyzed by SDS-PAGE and immuno blotting as described above. Purified protein may be concentrated to 1-2 mg per ml using a microconcentrator (Amicon) and these samples may be used to determine the specificity of the selected antibodies either by ELISA or by Isothermal Titration Calorimetry.

2. Large-Scale Monoclonal Antibody Production (In vitro Ascites—"IVA")

A series of positive clones (for their ability to identify both native and denatured antigen by methods of ELISA, dot blot and immuno blotting) are selected for large scale production on in vitro ascites. Cells are grown to high density in a vessel divided into compartments by a membrane, the CeLLine made by Integra Biosciences (Zurich, Switzterland), using serum free media, supplemented with additives that enhance antibody production.

3. Purification of Monoclonal Antibodies

Purification of monoclonal antibodies may be accomplished by affinity chromatography on 1-mL columns of Protein G-agarose (Sigma) in 1×10 cm Econocolumns (Bio-Rad) as described (David Lane, 1999). Typically, 500 mL of serum-containing supernatant is diluted with 1/10 volume 1 M Tris-Cl pH 8.0. The sample is run through the column at a flow rate of 0.8 ml/min controlled by Peristaltic Pump P-1 (Pharmacia LKB), followed by washes of 10 column volumes with 0.1 M Tris pH 8.0 and 10 column volumes of 10 mM Tris pH 8.0, at a flow rate of 0.8 mL/min. Antibody is eluted with 0.5 mL fractions of 50 mM glycine pH 3.0 into 1/10 volume 1 M Tris pH 8.0. Antibody-containing fractions are identified by observing optical density at 280 nm and confirmed by SDS-PAGE, then pooled and dialyzed against PBS with two changes of buffer, overnight at 4° C. Protein yield is determined by Bradford protein assay (Bio-Rad).

Example 10

Characterization and Quality Control of the Purified IgGs

Utilizing isothermal titration calorimetry and ELISA, antibodies may be characterized by the virtue of their binding isotherms with the recombinant protein.

1. Isothermal Titration Calorimetry

Commonly employed methods of analyzing antibody product quality, such as electrophoresis or chromatography characterize the molecular structure without providing information about binding activity. This is especially true in the evaluation of lot-to-lot variation of antibody function. Isothermal Titration Calorimetry (ITC) affords a much simpler and more accurate method for the quality control and characterization of antibodies and antibody products. ITC can be used to rapidly and effectively measure a wide range of physical characteristics, such as antibody affinity (Ka), the heat of antigen binding ($\Delta H$), and the apparent number of active binding sites (n) on an antibody or antigen. Changes in structure (fragmentation, partial denaturation, and modification by coupling agents) can be correlated to changes in binding affinity. In addition, heats of binding can be used as predictors of the antibody-antigen reaction both in vitro and in vivo.

In ITC, a solution of a ligand (e.g. a receptor, antibody, etc) is titrated against a solution of a binding partner at constant temperature. The heat released upon their interaction ($\Delta H$) is monitored over time. As successive amounts of the ligand are titrated into the cell, the quantity of heat absorbed or released is in direct proportion to the amount of binding occurring. As the system reaches saturation, the signal diminishes until only heats of dilution are observed. A binding curve is then obtained from a plot of the heats from each injection against the ratio of ligand and binding partner in the cell. Standard protocols are followed to determine the specificity and sensitivity of the purified antibodies using ITC. (Sawas et al, 2004).

2. ELISA for Antigen Detection

Polystyrene 96 well microtiter plates are coated at 4° C. overnight with purified recombinant antigen (PGDS) at 1 µg/ml (100 µl/well) in carbonate bicarbonate buffer (PH 9.6). The plates are washed twice with PBST and then blocked with 1% non-fat skim milk in phosphate-buffered saline (PH 7.4) containing 0.05% Tween 20 for 1 h at 37° C. Monoclonal antibodies with different dilutions in culture supernatant are added to the wells (100 µl/well) and plates will be incubated for 1.5 h at RT and 30 min at room temperature. The plates are then washed five times with PBST, 100 µl of anti-mouse HRPO (1:1000 in PBST) added, and plates incubated at 37° C. for another 30 minutes. After repeating the washing step as above, the enzyme activity may be assessed by incubation for 15 min at RT with 100 µl/well of TMB peroxidase substrate (Bio-Rad). After addition of 25 µl/well of 2.5 N H2SO4 to stop the reaction, the optical density at 450 nm may be measured with an automatic microplate reader.

Example 11

Lateral Flow Device to Identify CSF in Clinical Samples

The device of the present invention is implemented utilizing an immunochromatographic test based on the use of two monoclonal antibodies. The test device includes a test strip (for example, 0.8 cm-6.2 cm) with a plastic test cassette (FIG. 4). The antibodies are attached to three different zones on the membrane; a sample zone (S), a test zone (T), and a control zone (C). PGDS-mAb1 conjugated with latex particles is attached to the S-zone. PGDS-mAb2 is permanently immobilized to the T-zone, and the rabbit anti-mouse antibody is immobilized to the C-zone.

1. Conjugation of PGDS-mAb1 to Latex Particles

In one embodiment, the device of the present invention utilizes a first PGDS monoclonal antibody conjugated to a mobile particle, such as a latex particle (Magsphere Inc, Pasadena Calif.) or a gold particle (Bioassay Works, Ijamsville, Md.). The latex particles are preferably dyed blue and are made of polystyrene 0.3 mm in diameter. Latex particles (50 ml, 10% solution) are washed once in 2-Morpholinoethanesulphonic acid (MES) buffer, 50 mM pH 5.5, at room temperature. The pellet is resuspended in 600 ml phosphate-buffered saline (PBS, Sigma), pH 7.4, and mixed with 300 mg PGDS-mAb1. The suspension are mixed for 2 h at room temperature. The antibody-latex suspension is washed twice in Tris (-hydroxymethyl aminomethane) buffer, 100 mM, pH8.0, with 0.2% bovine serum albumin (BSA). The pellet is then resuspended in 500 ml Tris buffer and stored at 4° C. The conjugated suspension (100 ml) is applied by an automatic airbrush system (Bio-Dot Inc., Irvine, Calif.) onto a conjugate pad (0.5 cm-30 cm) and dried for 60 min at room temperature.

2. Immobilization of PGDS-Mab2 And Rabbit Anti-Mouse Antibodies

A second PGDS monoclonal antibody (PGDS-mAb2) and a rabbit anti-mouse antibody are also used in the device of the present invention. PGDS-mAb2 and rabbit anti-mouse antibodies at a concentration of 5 mg/ml may be applied with two automatic airbrush systems (Bio-Dot) as two separate lines onto a nylon membrane (4 cm-30 cm) with pore size of 5 mm purchased commercially. The membrane may be dried for 30 min and blocked with PBS (Sigma), pH 7.4, containing 0.25% casein for 15 min on a shaker. The membrane is dried at 37° C. for 60 min and stored in a sealed bag with desiccant (Esfandiari and Klingeborn, 2000).

3. Test Procedure

Referring now to FIG. 5, a small amount of PGDS containing sample is added to the S-zone. As shown in FIG. 5A, PGDS present in sample will bind to the latex conjugate and form a PGDS-conjugate-complex, and migrates chromatographically on the membrane. When the complex reaches the immobilized antibody in the T-zone, the bead-marker-Mab1 complex gets trapped onto the "T-zone: which is comprised of immobilized Mab2 and a blue colored band is formed. The result is an agglutination of the antigen-antibody complex along with the colored latex or gold beads on the "T-zone", which in turn causes the colored line to appear because of the entrapment of the beads. A blue band shown within 3-5 min in the T-zone indicates a positive result (FIG. 5A). No band in the T-zone is significant for a negative result (FIG. 5B). The immobilized polyclonal antibody in the C-zone will bind the latex conjugate with both positive and negative samples. This blue band assures a correct test performance.

4. Use of the CSF Detection Device

The device of the present invention may be utilized in a variety of clinical settings to determine the presence of Cerebral Spinal Fluid (CSF) in a sample. The devices use could be used for the detection of CSF in the following conditions (but not be limited to):

Skull Fractures with CSF leak (primarily base of skull fracture)
CSF leak following Endoscopic endonasal surgery
CSF leak following Neurosurgery
CSF leak following Epidural catheter placement
Spontaneous Intracranial Hypotension following CSF leak
Anthrax induced intracranial hypotension with CSF leak
CSF leak associated Rhinnorhea and Otorrhea
CSF leak associated with Hydrocephalus
CSF leak associated intracranial Neoplasms
CSF leak associated Congenital Neural Malformations While the invention has been described above with reference to specific embodiments thereof, it is apparent that many changes, modifications, and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A method for detecting the presence or absence of cerebrospinal fluid in a fluid sample from a needle placed in the epidural space to administer epidural medication or a fluid sample from a catheter attached to the needle, comprising
analyzing the fluid sample from a needle placed in the epidural space to administer epidural medication or the fluid sample from a catheter attached to the needle for binding with an antibody against lipocalin-type prostaglandin D2 synthase; and
correlating the presence or absence of binding with the antibody with the presence or absence of cerebrospinal fluid in the sample.

2. The method of claim 1, wherein the antibody is an antibody generated against a lipocalin-type prostaglandin D2 synthase peptide epitope.

\* \* \* \* \*